(12) United States Patent
Ouyang et al.

(10) Patent No.: US 12,117,382 B2
(45) Date of Patent: Oct. 15, 2024

(54) COMPACT GAS SENSING DEVICE AND THERMOSTATIC MODULE THEREOF

(71) Applicant: SHENZHEN CAMBRI ENVIRONMENTAL TECHNOLOGY CO. LTD., Guangdong (CN)

(72) Inventors: Bin Ouyang, Guangdong (CN); Ziqiang Guo, Guangdong (CN); Wenyu Li, Guangdong (CN); Yuzheng Wang, Guangdong (CN)

(73) Assignee: SHENZHEN CAMBRI ENVIRONMENTAL TECHNOLOGY CO. LTD., Guangdong (CN)

( * ) Notice: Subject to any disclaimer, the term of this patent is extended or adjusted under 35 U.S.C. 154(b) by 345 days.

(21) Appl. No.: 17/806,136

(22) Filed: Jun. 9, 2022

(65) Prior Publication Data

US 2023/0258547 A1     Aug. 17, 2023

(30) Foreign Application Priority Data

Feb. 11, 2022   (CN) .......................... 202210129040.0

(51) Int. Cl.
*G01N 1/44*      (2006.01)
*G01N 21/3504*   (2014.01)
(Continued)

(52) U.S. Cl.
CPC ........... *G01N 1/44* (2013.01); *G01N 21/3504* (2013.01); *G01N 27/64* (2013.01); *G01N 33/004* (2013.01)

(58) Field of Classification Search
CPC ...... G01N 1/44; G01N 21/3504; G01N 27/64; G01N 33/004; G01N 27/66;
(Continued)

(56) References Cited

U.S. PATENT DOCUMENTS 5,756,878 A      5/1998  Muto et al.
6,433,314 B1 *   8/2002  Mandrekar ............ G05D 23/19
                                                   219/390
(Continued)

FOREIGN PATENT DOCUMENTS

CN    204440190 U    7/2015
CN    110741253 A    1/2020
(Continued)

OTHER PUBLICATIONS

Communication pursuant to Article 94(3) EPC of EP Corresponding Application 22177297.3 issued on Nov. 29, 2023 from the EPO. (9Pages).
(Continued)

*Primary Examiner* — David P Porta
*Assistant Examiner* — Gisselle M Gutierrez
(74) *Attorney, Agent, or Firm* — Grossman, Tucker, Perreault & Pfleger, PLLC

(57) ABSTRACT

A thermostatic module of a compact gas sensing device and a compact gas sensing device are disclosed. The thermostatic module includes a housing unit, a thermal insulation unit, a heat conducting unit, a temperature sensor, a heater and a control circuitry board. The thermal insulation unit is placed inside a first accommodation space provided by the housing unit, and forms therein a second accommodation space in which the heat conducting unit is placed. The interior of the heat conducting unit forms a third accommodation space where gas sensor modules can be housed, and also a gas passage channel. The heater generates and transfers heat to the heat conducting unit, whose interior temperature is constantly probed by the temperature sensor and input to the control circuitry board which dynamically adjusts the heating power by the heater to make sure the
(Continued)

measured temperature is always stabilized around a preset target value.

14 Claims, 3 Drawing Sheets

(51) Int. Cl.
*G01N 27/64* (2006.01)
*G01N 33/00* (2006.01)

(58) Field of Classification Search
CPC ....... G01N 33/0009; G01N 2201/0231; G01N 33/0004; G05D 23/19; H05B 1/0202; H05B 1/023; H05B 3/02; H05B 3/04
See application file for complete search history.

(56) References Cited

U.S. PATENT DOCUMENTS

| | | | |
|---|---|---|---|
| 2009/0095918 A1* | 4/2009 | Iwase | G01N 21/031 73/23.31 |
| 2016/0153929 A1* | 6/2016 | Rottmann | G01M 15/104 73/31.05 |
| 2020/0003738 A1* | 1/2020 | Schmittmann | G01N 30/6095 |

FOREIGN PATENT DOCUMENTS

| | | |
|---|---|---|
| CN | 210894267 U | 6/2020 |
| CN | 213300479 U | 5/2021 |
| CN | 213580569 U | 6/2021 |
| CN | 213933758 U | 8/2021 |
| EP | 0724151 A1 | 7/1996 |
| EP | 3139160 A1 | 3/2017 |
| JP | H085552 A | 1/1996 |
| JP | 2015087146 A | 5/2015 |

OTHER PUBLICATIONS

Application Study of Constant Temperature Heating Equipment on Fog Tester, vol. 40, No. 06-2013-12-31, author Ye Wanshui. (7 pages).
Equipment Engineering, First Edition-Aug. 31, 2005, author Yang Xiuqin et al. (8 pages).
First Office Action from priority application CN 202210129040.0 issued on Jun. 7, 2024 by CNIPA. (5 pages) (english translation attached 6 pages).
First Search-Patent Search Records Information from priority application CN Application No. 202210129040.0. (2 pages).

* cited by examiner

COMPACT GAS SENSING DEVICE AND THERMOSTATIC MODULE THEREOF

CROSS-REFERENCE TO RELATED APPLICATIONS

The present application claims the priority of Chinese Patent Application No. 202210129040.0 entitled "COMPACT GAS SENSING DEVICE AND THERMOSTATIC MODULE THEREOF" and filed by the applicant on Feb. 11, 2022, which is hereby incorporated by reference in its entirety.

FIELD

The present disclosure relates to the field of sensing technology, and more particularly, to a compact gas sensing device and a thermostat module thereof.

BACKGROUND

Currently, air quality and its effects on health are drawing more and more attention, and the measurement for trace components in the air is becoming increasingly important. A compact gas sensor is an important tool for monitoring important gas molecules, especially trace gaseous pollutants in both the indoor and outdoor environments. Compact sensor technology has many advantages such as small space occupation, light weight, low power consumption and low cost, and therefore is suitable to be widely distributed to acquire related data in terms of the emission sources, the dispersion pattern and the population exposure characteristics of gas molecules especially those of the pollution gases with ultrahigh temporal and spatial resolution.

Volatile organic compounds (VOCs) in the air can be taken as an example. Under solar radiation, VOCs can undergo a series of complicated photochemical reactions with nitric oxides to produce ozone which, once inhaled, can have strong negative effects on human respiratory and cardiovascular systems due to its strong oxidizing property. Ambient ozone concentration therefore is one of the important factors in determining air quality. Some VOCs in the indoor environment, such as formaldehyde and the aromatic compounds including benzene, methylbenzene and xylene all have known carcinogenic, teratogenic and other harmful effects. When ventilation in an indoor environment is poor, these VOCs may evaporate slowly from products such as furniture and paint of inferior quality, concentrate and reach a level that is above the standard for indoor air quality and produce harmful health effects on the dwellers. Besides, the VOCs may be oxidized gradually in the air and generate organic products with lower vapour pressures. These organic products may then get into the aerosol phase through a series of processes including condensation, nucleation and coagulation, contributing to the increase in weight and number density of particles. Based on the above, an accurate and precise measurement of concentration of VOCs can help to locate areas with high VOCs concentrations timely and inform people of potential exposure risks. Further, in conjunction with multidimensional data information including the temporal and spatial distributions of VOCs concentrations, climate and atmospheric dispersion conditions, the emission or leaking sources of VOCs can be accurately located, and the non-compliant emission sources of VOCs can be effectively managed and regulated, so as to reduce the total emission of VOCs and their potential for generating ozone and secondary organic aerosols.

However, the composition of VOCs in the air can be quite complex, which includes alkanes, alkenes, alkynes, aromatics and VOCs containing nitrogen, oxygen and sulphur, and all these may have totally different physical and chemical properties. In a common laboratory analysis, the VOCs are usually pre-separated using a gas chromatographic column, and then are examined qualitatively or quantitatively using a mass spectrometer detector, a flame ionization detector, a photo ionization detector or other ionization and detection techniques. These methods can identify and quantify individual VOCs, but the analytical instruments used require relatively stable operational environments along with a continuous supply of consumables (such as carrier gas in chromatography), thereby resulting in high costs, relatively complicated operation procedures, large space demand and heavy instrument weights. Meanwhile, since the sample introduction, enrichment and separation through a chromatographic column all take some time, the measured data tend to be discontinuous and can result in missing a strong emission signal that lasts only a brief period of time.

Since the VOC sources in an environment can be numerous (such as combustion in industrial processes and automobile engines, painting, dye spraying and evaporation from storage facilities and oil tanks), fugitive sources tend to make a large contribution to the total emitted VOCs. For this reason, monitoring networks with dense distribution of sensing nodes are needed in order to accurately locate the VOCs emission sources, whilst the above laboratory-grade analytical instruments often find limited or no use in these areas. In brief, users and operators need a sensor-based instrument with smaller size, lower power consumption, lower cost and higher levels of readiness for use, in order to perform VOCs measurements through high-density monitoring networks. The use of sensors makes the component analysis of VOCs no longer feasible, but on the other hand bears the competitive advantage of offering a much wider, detailed and hence more representative coverage of VOCs emission signatures/footprints at unprecedented spatio-temporal resolutions.

Photo Ionization Detector (PID) sensors can detect VOCs at ultra-low concentrations (to ppb levels). Its detection principle is well known—gas samples are illuminated by short-wavelength ultraviolet light from a lamp source, during which the VOC components get photo-ionized and the resulting ions are collected by an electrode stack to give an electrical signal whose intensity is directly proportional to the VOC concentration in the air, and the VOC concentration can then be derived. PID sensors have many characteristics/advantages over the other VOCs measurement techniques. First, they are small in size and consume little power, and VOCs analytical instruments based on the PID detection principle also enjoy these two advantages. Secondly, PID can respond to a wide range of VOC species, in particular those with relatively high photochemical activities/OH reactivities, and moreover the detectable VOCs range can be adjusted/augmented depending on the lamp source used. Thirdly, PID requires no gas or liquid consumables, and can operate in the outdoor environment for a long period of time without much intervention (such as continued replenishment of consumables). Based on the above, PID is one of the most suitable techniques for forming dense VOCs monitoring networks.

However, if one defines the baseline of the PID sensor to be "the reading of the sensor in real time under changing temperature and relative humidity of the environment when, however, no detectable VOCs is contained in the air", it has been noted that such baseline can change significantly which suggests that these two environmental factors can strongly affect the working of the PID sensor. Such undesirable signal then mixes with the signal induced by VOCs in the environment and severely affects the accuracy of VOCs measurements.

Another typical air pollutant is carbon dioxide ($CO_2$). $CO_2$ in the outdoor air mainly comes from the combustion of fossil fuel which often emits NOR, particles, CO and $SO_2$ simultaneously; all these species can have negative effects on human health. $CO_2$ in the indoor environment mainly comes from people's breath, and on top of that may also arise from the indoor combustion of the various fossil fuels. When the indoor $CO_2$ concentrations are high, it often indicates that human density is too high or that ventilation is not sufficient, and intervention measures such as an improved ventilation and/or reduced room occupancy/fuel combustion are needed. Since $CO_2$ absorbs certain bands of infrared light strongly, its monitoring is mainly achieved through infrared absorption spectroscopy including e.g. cavity ringdown-based absorption spectroscopy, which typically yields an extremely high measurement precision at the expense of complicated instrumentation and therefore high cost, and the less precise but much more convenient and cost-friendly non-dispersive infrared absorption (NDIR) spectroscopy. Like the PID sensors, the "baseline" of NDIR $CO_2$ sensors is also subject to significant drifts, since the radiation spectrum of its light source, the light response curve of its detector, and expansion/shrinkage of its housing material may all change with temperature, thereby bringing changes to the intensity of the transmitted light signal. Since NDIR derives the $CO_2$ concentration from the change in the transmitted light intensity, any perturbation to the latter caused by ambient temperature change will produce a false $CO_2$ concentration signal, deteriorating measurement accuracy.

SUMMARY

The present disclosure aims to solve at least one of the technical problems in the prior art. To this end, one aim of the present disclosure is to provide a thermostatic module of a compact gas sensing device, which can improve the stability and accuracy of the measurement of concentrations of trace components in the air performed by the compact gas sensing device.

The present disclosure further provides details about a compact gas sensing device.

The thermostatic module of a compact gas sensing device according to the present disclosure includes a housing unit, a thermal insulation unit, a heat conducting unit, a heater, a temperature sensor and a control circuitry board. The inside of the housing unit forms the first accommodation space. The thermal insulation unit is placed within the first accommodation space and its hollow interior forms the second accommodation space. The heat conducting unit is placed within the second accommodation space. The inside of the heat conducting unit forms the third accommodation space, which contains a gas passage channel and the gas sensor itself. The heater is provided on the surface of the heat conducting unit to generate and then transfer heat to the heat conducting unit. The temperature sensor is provided inside the heat conducting unit to measure temperature inside the heat conducting unit continuously. The control circuitry board is electrically connected with the heater and is configured to generate a control signal based on the difference between the temperature measured and the preset target temperature, so as to keep the temperature inside the heat conducting unit stabilized at the target temperature all the time.

Based on the above principle, the temperature sensor measures the temperature inside the heat conducting unit, which the control circuitry board then uses to adjust the heating power of the heater so as to keep the reading of the temperature sensor stabilized at the target temperature value. The control circuitry board may adopt the Proportional-Integral-Derivative algorithm in which the heating power of the heater is determined by the current difference between the measured temperature in the heat conducting unit and the preset target temperature (corresponding to the proportional term), the integrated past difference over a selected period of time between the two temperature values (corresponding to the integral term), and the rate of change of the difference (corresponding to the derivative term). In this way, the heating power of the heater is set to increase when the measured temperature is lower than the target value, and to decrease when the opposite is true, essentially forming an effective negative feedback loop through which the temperature inside the heat conducting unit can be kept constant. Meanwhile, the incoming gas sample has its temperature raised during its flow in the gas passage channel to the same value as that in the third accommodation space, to prevent a cold island from being formed in the third accommodation space after the gas sample flows in, which can disturb the temperature of the embedded PID sensor and affects its measurement accuracy.

In some examples of the present disclosure, the gas passage channel includes an inlet part and an outlet part, where the inlet part is the channel through which the sample gas enters the third accommodation space and gets detected by the PID sensor therein, and the outlet part is the channel through which the sample gas leaves the third accommodation space, and the third accommodation space is, as can be seen, between the inlet and outlet parts.

In some examples of the present disclosure, the inlet passage channel part adopts a sinuous path to realize a longer residence time within the limited volume in the thermal conductor, to allow for a more sufficient heat exchange between the gas and the thermal conductor.

In some examples of the present disclosure, the inlet passage channel includes a plurality of straight segments and a plurality of arc-shaped connection segments, in which the the plurality of straight segments can be placed in parallel, and each of the plurality of arc-shaped connection segments is set to join its two adjacent straight segments.

In some examples of the present disclosure, the housing unit includes a first housing unit and a second housing unit, the heat-insulation unit includes a first heat-insulation unit and a second thermal insulation unit, and the heat conducting unit includes a first heat conducting unit and a second heat conducting unit. The first thermal insulation unit is provided in the first housing unit, the first heat conducting unit is provided in the first thermal insulation unit, the second thermal insulation unit is provided in the second housing unit, the second heat conducting unit is provided in the second thermal insulation unit, and the first heat conducting unit and the second heat conducting unit are then combined, with the inner hollow volume defining the third accommodation space and the gas passage channel.

In some examples of the present disclosure, a first sealing member made of typical elastic O-ring materials is compress-fitted between the first heat conducting unit and the second heat conducting unit, to form a good seal around the perimeter of the joining faces of the two heat conducting units and prevent gas leakage into the gas passage channels/third accommodation space from outside through such perimeter.

In some examples of the present disclosure, the thermostatic module of the compact gas sensing device further includes a gas pump connected with the gas passage channel.

In some examples of the present disclosure, the heater is in the form of electrical heating sheets, bands or wires, and is attached to the surface of the heat conducting unit.

In some examples of the present disclosure, assuming that the temperature within the third accommodation space is T1 when the heating is completely off, while the preset target temperature is T2, then T2 and T1 must always satisfy T2>T1. In other words, there must always be a need to heat up the system for the range of environment in which the gas sensing device is deployed.

A compact gas sensing device according to the present disclosure is further provided. The compact gas sensing device includes the above-mentioned thermostatic module and a gas sensor module. The gas sensor module comprises the sensor itself as well as its supporting power supply and signal transmission circuitry board, and both are to be accommodated inside the third accommodation space.

In some examples of the present disclosure, a power cable is provided between the heater and the control circuitry board, and this cable has one end electrically connected with the control circuitry board and the other end passing through the housing unit and the thermal insulation unit and electrically connected with the heater.

In some examples of the present disclosure, the power supply and signal transmission circuit board of the gas sensor is connected to an external power supply and signal acquisition system through another set of wires, to facilitate any power and signal transmission between the two. A second sealing member made of suitable elastic rubber materials is provided between these wires and the heat conducting unit, to seal the passage hole of the wires through the heat conducting unit.

Additional aspects and advantages of the present disclosure will be given partially in the following description, or become apparent partially from the following description, or can be learned from practice of the present disclosure.

BRIEF DESCRIPTION OF DRAWINGS

The above and/or additional aspects and advantages of the present disclosure will become apparent and easy to understand from the description of embodiments below in conjunction with the accompanying drawings, in which.

DETAILED DESCRIPTION

Embodiments of the present disclosure will be described in further details below. The embodiments described with reference to the drawings are exemplary.

A thermostatic module 100 of a compact gas sensing device 1000 according to an embodiment of the present disclosure will be described below with reference to FIGS. 1-3.

Figure 1:
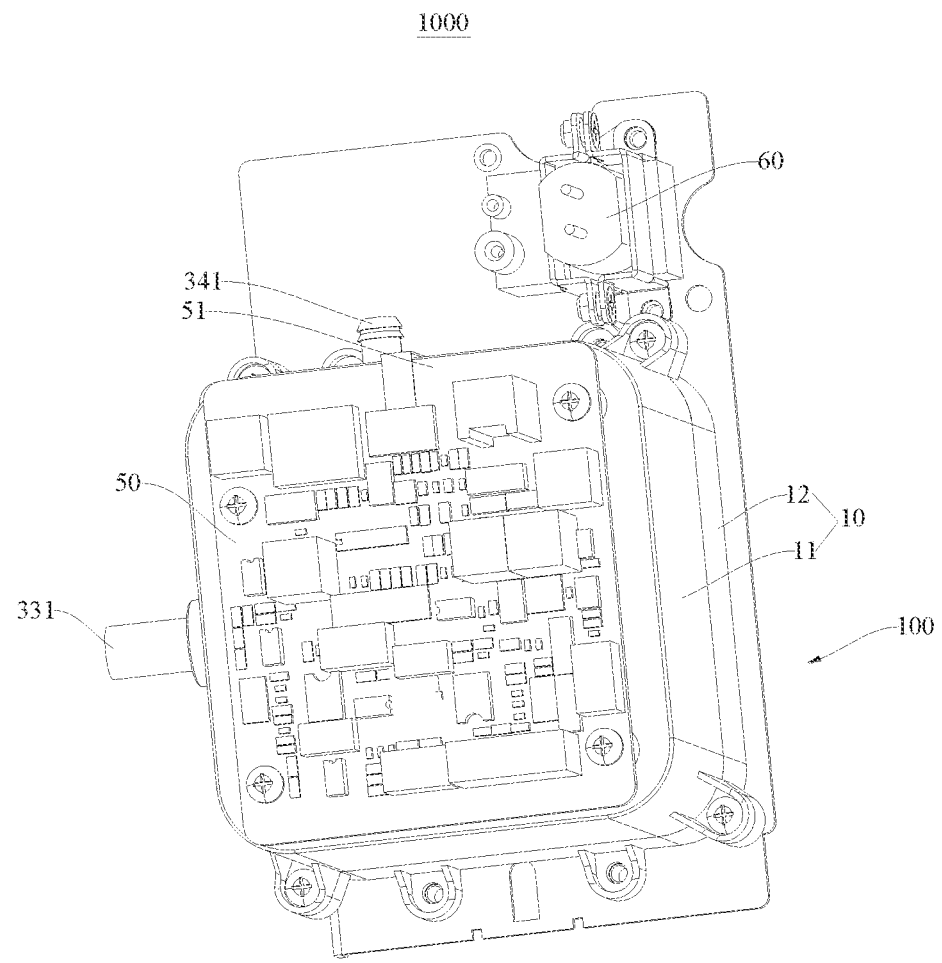
FIG. 1 is a schematic drawing illustrating a compact gas sensing device according to an embodiment of the present disclosure.
Figure 2:
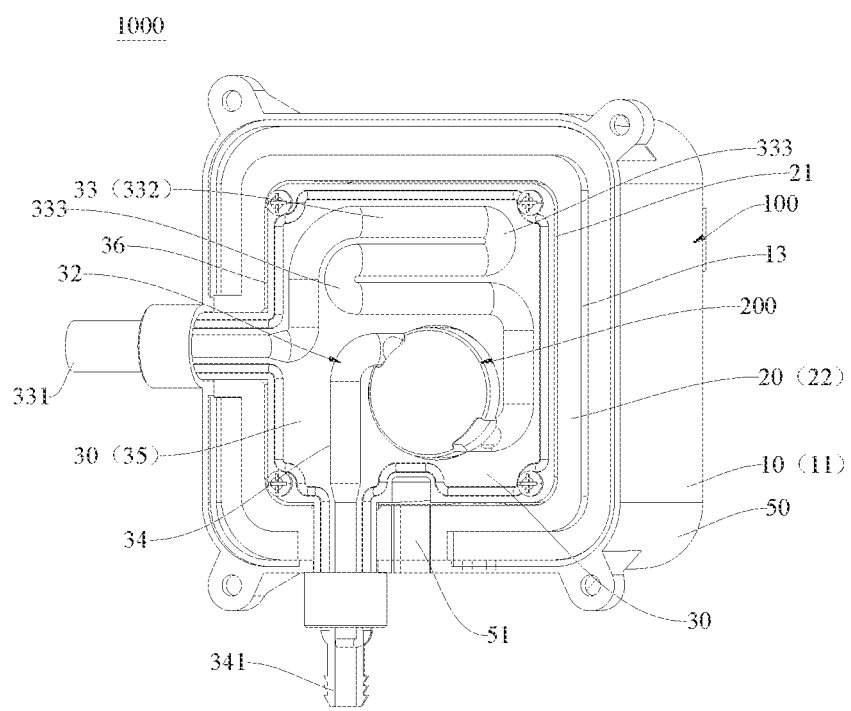
FIG. 2 is a schematic drawing illustrating a cross section of the compact gas sensing device as that shown in FIG. 1 according to an embodiment of the present disclosure.
Figure 3:
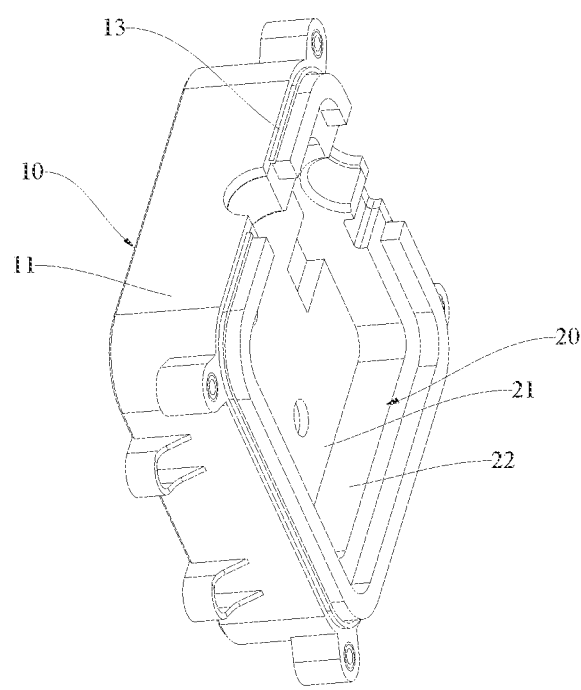
FIG. 3 is a schematic drawing illustrating the first housing and thermal insulation units of the compact gas sensing device as that shown in FIG. 1 according to an embodiment of the present disclosure.

As shown in FIGS. 1-3, the thermostatic module 100 of a compact gas sensing device 1000 according to the present disclosure mainly includes a housing unit 10, a thermal insulation unit 20, a heat conducting unit 30, a heater, a temperature sensor and a control circuitry board 50. The inside of housing unit 10 forms the first accommodation space 13, and the thermal insulation unit 20 is provided within the first accommodation space 13. The inside of the thermal insulation unit 20 forms the second accommodation space 21, and the heat conducting unit 30 is provided within the second accommodation space 21. The heater is provided on the heat conducting unit 30 to generate and transfer heat to the heat conducting unit 30. Housing unit 10 can protect the thermal insulation unit 20 and the heat conducting unit 30 from being corroded by external foreign matters and from being directly hit by an external force, so as to prevent damage and preserve structural integrity.

Further, by placing the heat conducting unit 30 within the second accommodation space 21 in the thermal insulation unit 20, after the heater starts to operate and transfer heat to the heat conducting unit 30, the thermal insulation unit 20 will prevent heat from being dissipated too rapidly to environment, which would otherwise cause an excessively high thermal loss and therefore an excessively high energy consumption by the heater, and could also lead to a poor temperature stability of the heat conducting unit 30 due to the potentially strong thermal coupling between the heat conducting unit and the external environment. In this way, the performance of the thermostatic module 100 is greatly improved.

It needs to be pointed out that, the heat conducting unit 30 should be made of material with excellent thermal conductivity. This way, the heat generated by the heater can be more quickly transferred to, and ultimately be uniformly distributed within the entire block of the heat conducting unit 30, and the temperature gradient across the heat conducting unit 30 can be small. Furthermore, the heat conducting unit 30 needs to be made of materials which are easy to machine and reasonable in cost so that they can be mass-produced. In particular, the heat conducting unit 30 may be made of metal such as aluminium or copper, metal alloy such as aluminium-magnesium, aluminium-copper or aluminium-silicon alloy, or non-metallic materials such as thermally conductive ceramic.

As shown in FIG. 2, the heat conducting unit 30 is machined to have a gas passage channel 32 and a third accommodation space in which a gas sensor module 200 is accommodated, and the gas passage channel 32 is connected with the third accommodation space. In particular, when the heater transfers heat to the heat conducting unit 30, the temperature of the third accommodation space in the heat conducting unit 30 rises and can finally be stabilized at a preset target value. Further, since the third accommodation space is used for accommodating the gas sensor module 200, the temperature of the gas sensor 200 will then also be kept constant, and the baseline reading of the gas sensor module 200 as controlled by temperature will remain stable and be least affected by any external temperature variations. The measurement of the target gas concentration by the gas sensor module 200 can then be more accurate and reliable. At the same time, the temperature of the gas passage channel 32, since it is embedded within the heat conducting unit 30, also rises and stabilizes at the preset temperature. After the gas enters the gas passage channel 32, it will be heated and an appropriately designed gas passage channel 32 and an appropriately selected gas flow rate, which together determines the residence time of the sample gas within the channel, can guarantee that the sample gas be heated for a sufficient amount of time so that it can reach the same temperature as that of the heat conducting unit 30, thereby preventing a cold island/chilling effect from occurring which can upset the gas sensor module 200 and its measurement.

The control circuitry board 50 which is shown in FIG. 1 is electrically connected with the heater and can adjust the heating operation of the heater. When the thermostatic module 100 of the compact gas sensing device 1000 starts to operate, a target temperature value is preset, and the heater will heat up the heat conducting unit 30 until the temperature measured by the temperature sensor built in the heat conducting unit 30 reaches the preset target value. A common control algorithm that one may use in this case is the Proportional-Integral-Derivative. In this control method, the heating power of the heater is determined by the current difference between the present temperature measured by the temperature sensor built in the heat conducting unit and the preset target temperature value (corresponding to the proportional term), the integrated past difference over a selected period of time between the two temperature values (corresponding to the integral term), and the rate of change of the difference (corresponding to the derivative term). In this way, broadly speaking the heating power of the heater is controlled to be increased when the measured temperature is lower than the target temperature value, and is lowered otherwise. Therefore, the temperature inside the heat conducting unit 30 will be kept stable via an effective negative feedback loop.

With the above, the thermal insulation unit 20 can efficiently slow down any heat exchange between the heat conducting unit 30 and the outside environment, thereby reducing the level of difficulty in regulating the temperature and also reducing the power consumption of the thermostatic module 100 of the compact gas sensing device 1000, which is of great significance for the implementation of the present disclosure in particular in an environment with limited power supply. Above all, the present disclosure provides a stable temperature environment for the gas sensor module 200, and thereby greatly improves its measurement accuracy and long-term stability. Here, the thermal insulation unit 20 can be made of heat retaining foam or plastic with low thermal conductivity coefficients.

In reality, due to the influence of non-negligible heat transfer time, time delay of the control logic, uncertainties in the temperature measurements by the built-in temperature sensor as well as some other possible environmental factors, it is not possible that the temperature as measured by the temperature sensor could be kept at exactly the target temperature value without any deviation. Often, the difference between the two can be controlled to be within about ±0.1° C., but we elect not to specify too precise a value here. Technically speaking, it is more desirable if a smaller difference between the two can be achieved.

As shown in FIG. 2, the gas passage channel 32 includes an inlet passage channel 33 and an outlet passage channel 34. The inlet passage channel 33 is connected with a gas inlet 331, the outlet passage channel 34 is connected with a gas outlet 341, and the third accommodation space sits between the two. In particular, by placing the third accommodation space between the inlet passage channel 33 and the outlet passage channel 34, after the sample gas enters the inlet passage channel 33 from the gas inlet 331, the inlet passage channel 33 will heat the gas to the same temperature as that of the heat conducting unit 30, and then the preheated gas enters the third accommodation space and gets detected by the gas sensor module 200. The preheating of the incoming gas within the inlet passage channel 33 is needed to avoid the interior of the third accommodation space from being in contact with cold air so as to avoid a cold island from being formed within, thereby preventing any likely drift of the baseline of the gas sensor module 200 due to temperature variations.

Furthermore, after the detection of the sample gas by the gas sensor module 200, the exhaust gas will be pumped from the third accommodation space through the outlet passage channel 34 and gas outlet 341 to the external environment. In this way, the gas flowing into the thermostatic module 100 of the compact gas sensing device 1000 is refreshed continuously, avoiding the detection result from being influenced by any residual gas within the third accommodation space.

Accordingly, by placing the heater on the heat conducting unit 30 and the heat conducting unit 30 inside the second accommodation space 21 of the thermal insulation unit 20, and using the control circuitry board 50 to regulate the heating operation of the heater, the heater can generate and transfer heat to the heat conducting unit 30 in a controlled manner such that the temperature of the heat conducting unit 30 will be maintained within a narrow but stable range, which will in turn provide a stable temperature environment for the working gas sensor module 200. Meanwhile, when the sample gas is pumped through the gas passage channel 32 into the third accommodation space, it will be heated up and its temperature will rise to the same value as that of the heat conducting unit. This way, the formation of possible cold islands in the third accommodation space can be prevented, which would otherwise cause undesirable temperature variations of the gas sensor module 200 within the third accommodation space and thus influence the accuracy of the measurement result.

As shown in FIG. 2, the inlet passage channel 33 adopts a sinuous path such that its length and volume can be maximized within the finite space in the thermostatic module 100. In this way, the residence time of the gas in the gas passage channel 32 can be extended and the contact between the two enhanced, thereby achieving a sufficient heating of the incoming sample gas and also optimizing the structural design of the thermostat module 100.

Referring to FIG. 2, the inlet passage channel 33 includes a plurality of straight segments 332 and arc-shaped connection segments 333. The straight segments 332 are arranged in parallel to each other, while each of the arc-shaped connection segments 333 joins its two adjacent straight segments 332. By arranging the straight and arc-shaped segments 332 and 333 this way, the length of the inlet gas passage channel 33 is extended, so the residence time of the gas in this part of the gas passage channel is lengthened and the contact between the two enhanced, which ensures a sufficient heating of the gas within the finite space inside the thermostatic module 100.

As shown in FIGS. 1-3, the housing unit 10 includes a first housing unit 11 and a second housing unit 12, the thermal insulation unit 20 includes a first thermal insulation unit 22 and a second thermal insulation unit, and the heat conducting unit 30 includes a first heat conducting unit 35 and a second heat conducting unit. The first thermal insulation unit 22 is provided inside the first housing unit 11, the first heat conducting unit 35 is provided inside the first thermal insulation unit 22, the second thermal insulation unit is provided in the second housing unit 12, the second heat conducting unit is provided in the second thermal insulation unit, and the first heat conducting unit 35 and the second heat conducting unit are assembled opposite to each other and collectively define the third accommodation space and the gas passage channel 32. In particular, the first thermal insulation unit 22 is provided in the first housing unit 11, the second thermal insulation unit is provided in the second housing unit 12, and the first thermal insulation unit 22 and the second thermal insulation unit together enclose the heat conducting unit 30. After the first housing unit 11 and the second housing unit 12 are combined, the first thermal insulation unit 22 and the second thermal insulation unit are aligned and fixed together. In this way, the structure of the third accommodation space and the gas passage channel is robust and the thermostatic module 100 of the compact gas sensing device 1000 can be assembled and manufactured conveniently.

It can be seen that the first heat conducting unit 35 and the second heat conducting unit each contains a half of the third accommodation space and a half of the gas passage channel 32. After the first housing unit 11 and the second housing unit 12 are combined and the first heat conducting unit 35 and the second heat conducting unit are assembled opposite to each other, the third accommodation space and the gas passage channel 32 are formed.

As shown in FIG. 2, a first sealing member 36 is provided between the first heat conducting unit 35 and the second heat conducting unit, to form a good seal along the perimeter of the joining faces of the two heat conducting units. The first sealing member 36 should be made of suitable elastic rubber materials in order to form good seals between the first heat conducting unit 35 and the second heat conducting unit when compressed. In particular, the first sealing member 36 is provided between the first heat conducting unit 35 and the second heat conducting unit, and after the two units are assembled together, the first sealing member 36 can be compressed and therefore seals.

The purpose of the first sealing member 36 is to prevent the external gas from entering the third accommodation space through any gap between the first heat conducting unit 35 and the second heat conducting unit rather than through the inlet passage channel 33. In this way, it is guaranteed that the sampled gas always comes from the external environment and is heated right to the target temperature, thus improving the structural robustness and reliability of the thermostatic module 100 of the compact gas sensing device 1000.

As shown in FIG. 1, the thermostatic module 100 of the compact gas sensing device 1000 further includes a gas pump 60 connected with the gas passage channel 32, which is used to pull external air through the gas inlet 331 and the gas passage channel into the third accommodation space where it is then detected by the gas sensor module 200.

After the external gas enters the gas passage channel 32 from the gas inlet 331, it needs to be fully preheated to the preset target temperature before entering the third accommodation space and detected by the gas sensor module 200, so as to prevent the temperature of the gas sensor module 200 from being influenced by the external gas if it is of a lower temperature. Here, a heating passage can be machined upstream of the third accommodation space in the thermostatic module 100 in the compact gas sensing device 1000, so that the preheating of the gas can be conveniently done therein and using the heat from the heater itself instead of having to introduce any extra preheater, thereby simplifying the structure of the thermostatic module 100 of the compact gas sensing device 1000. Furthermore, any gas flowing through the gas passage channel 32 can be heated to the same temperature as that of the third accommodation space, thereby minimizing the potential temperature difference between the sample air and the gas sensor module 200 and reducing the disturbance of this temperature difference to the reading of the gas sensor module 200.

In some other embodiments of the present disclosure, however, the gas can be preheated by a separate preheating tube provided outside the thermostatic module 100 of the compact gas sensing device 1000, and different designs of the preheating tube may use gas pumps 60 with different flow capacities (the gas flow rate can be adjusted by, e.g. varying the voltage setting of the pump) and gas passage channels 32 with different diameters and lengths. In this case, the residence time of the gas in the gas passage channel 32 needs to be calculated based on the gas flow rate and the internal dimensions of the gas passage channel 32, and moreover thermal simulations can be performed for the residence time and structural design, so as to ensure that the residence time as well as thermal contact is enough for the external gas to be preheated to the target temperature value.

Further, the heater can either be heating sheet or heating wires, and is attached on the heat conducting unit 30. In particular, good thermal contact between the heater and the heat conducting unit 30 can be achieved by applying thermal paste or adhesive in between and/or applying pressure, and since the heat conducting unit 30 has good thermal conductivity, the heat from the heater can be readily transferred to the third accommodation space and the gas passage channel 32 through thermal conduction. In this way, the heater does not sit too close to the gas sensor module 200 and the heat distribution also tends to be uniform inside the third accommodation space and the gas passage channel 32, which effectively prevents any overheating of and damage to the gas sensor module 200. This structural design of the thermostatic module 100 of the compact gas sensing device 1000 is thus more optimal.

Further, selection of the heating element for the heater depends on the size and shape of the thermostatic module 100 of the compact gas sensing device 1000, cost, ease of assembly and detailed application environment, and may use heating sheet or heating wires as candidates. Further, the maximum heating power of the heater needs to guarantee that, when the external environment temperature reaches the minimum value during the measuring period, i.e., when the thermostatic module 100 of the compact gas sensing device 1000 dissipates heat most rapidly, the preset target temperature value can still be reached through heating by the heater.

Further, assuming that the temperature sensor built in the third accommodation space measures a temperature of T1 when the heating by the heater has been entirely switched off, while the target temperature value of the heater which is preset by the control circuitry board 50 is T2, then T2 and T1 must always satisfy T2>T1. Specifically, the target temperature value T2 can be set according to the user's need, but must be reached through heating rather than cooling. This is at least based on the two following considerations. First, a versatile temperature control unit having both cooling and heating capabilities is considerably more complicated, difficult and costly to design and produce than the one that has only heating capacity. Second, a higher T2 can always avoid water vapour condensation within the heat conducting unit 30, which would otherwise cause instability of the measurement performed by or even damage to the gas sensor module 200. Meanwhile, the preset target temperature value shall not go beyond the upper limit of the normal working temperature range of the gas sensor module 200 to avoid potential damage to the sensor by the high temperature applied. A specific target temperature value may be determined by an experienced user of the compact gas sensing device 1000 according to the humidity of the actual operating environment, season and others.

As shown in FIG. 1, a compact gas sensing device 100 according to an embodiment of the present disclosure mainly includes the above mentioned thermostatic module 100 of the compact gas sensing device 1000 and the gas sensor module 200. The gas sensor module 200 is placed in the third accommodation space. Further, the gas sensor module 200 is fitted with a power supply and signal transmission circuitry board, and both the gas sensor module 200 and its power supply and signal transmission circuit board are placed within the third accommodation space. This way, after the thermostatic module 100 in the compact gas sensing device 1000 starts to operate, the temperature in the third accommodation space will be kept at a relatively stable value, such that the gas sensor module 200 is always in an environment with a relatively constant temperature, and the measurement result thereof becomes more accurate. When the gas sensor module 200 detects VOCs in the air and generates an electrical current, the signal transmission circuitry board for the gas sensor module 200 processes and converts the electrical current to voltage and transmits the converted electrical signal to a system connected with the power supply and signal transmission circuitry board for reading and viewing by the user.

It is noteworthy that the gas sensor module 200 can be any appropriate sensor type, such as a Photo Ionization Detector (PID) or an NDIR (Non-Dispersive Infrared) $CO_2$ sensor which needs to be placed in air to measure the concentration(s) of certain component(s) therein. By placing the gas sensor module 200 in the thermostatic module 100 of the compact gas sensing device 1000, the effect of changing ambient temperature on the performance of the gas sensor can be minimized, improving the accuracy of the measurement outcome.

Moreover, the above PID and NDIR-based $CO_2$ sensors are photoelectric sensors, and main internal parts thereof include a light source, an ion collecting electrode (for the PID sensor), an optical detector (for the NDIR sensor) and necessary connection wires etc. These internal parts still work normally in a heated environment above the common ambient temperature and their lifetimes will not be considerably affected, which suggests that these sensors can stand the relatively high T environment, and the thermostatic module 100 as described above can serve as an effective way of eliminating the potentially strong temperature effect of these gas sensors. Some other gas sensor modules may not necessarily satisfy the above conditions, and for this reason cannot be thermally stabilized at elevated T. Take the electrochemical gas sensors as an example—these sensors often contain high-concentration liquid electrolyte which tends to evaporate when heated, thus disabling the normal functioning of the sensors.

Furthermore, if the adsorption or chemical reactivity of the molecules to be measured is strong on the surface of the heat conducting unit 30, these surfaces which are in direct contact with the sample air can/should be coated with polytetrafluoroethylene (PTFE) or be silanized in order to minimize such effects. It then also becomes obvious that when choosing the material for making the heat conducting unit 30, one must consider if it is amenable to such pretreatment as PTFE coating or silanization.

As shown in FIG. 2, a first electric cable 51 is provided between the heater and the control circuitry board 50. The first electric cable 51 has one end electrically connected with the control circuitry board 50, and the other end passing through the housing unit 10 and the thermal insulation unit 20 and electrically connected with the heater. In this way, the electrical connection between the heater and the control circuitry board 50 is simple and robust.

As shown in FIG. 1 and FIG. 2, a second electric cable is provided between the power supply and signal transmission circuit board of the gas sensor module 200 and the external power supply and data acquisition system. The second electric cable has one end electrically connected with the power supply and signal transmission circuit board, and the other end passing through the housing unit 10, the thermal insulation unit 20 and the heat conducting unit 30 and electrically connected with the external power supply and data acquisition system. Further, a second sealing member made of typical elastic rubber materials is provided between the second electric cable and the heat conducting unit 30 to prevent gas from entering the third accommodation space through the gap between the two. In this way, the seal and reliability of the sampling structure of the compact gas sensing device 1000 is improved.

In the description of the present disclosure, it shall be understood that, terms such as "center", "longitudinal", "crosswise", "length", "width", "thickness", "up", "down", "front", "rear", "left", "right", "vertical", "horizontal", "top", "bottom", "inside", "outside", "clockwise", "counterclockwise", "axial", "radial", "perimeter" and others illustrating orientational or positional relations, are all on the basis of the orientational or positional relations illustrated in the drawings for convenience or simplicity of the description of the present disclosure, do not indicate or imply that the devices or elements must have a specific orientation or must be constructed and operated in a specific orientation and thus cannot construed as limiting the present disclosure.

In the description of the present disclosure, the description with reference to the terms "one embodiment", "some embodiments", "exemplary embodiments", "example", "specific example", or "some examples", etc., means that specific features, structures, materials, or characteristics described in conjunction with the embodiment(s) or example(s) are included in at least one embodiment or example of the present disclosure. In the present disclosure, any illustrative reference to the above terms does not necessarily refer to the same embodiment(s) or example(s).

Although the embodiments of the present disclosure have been shown and described above, it can be appreciated by those of ordinary skill in the art that various changes, modifications, replacements and variants can be made to the above embodiments without departing from the principle and the spirit of the present disclosure. The scope of the disclosure is defined by claims and equivalents thereof.

What is claimed is:
1. A thermostatic module of a compact gas sensing device, comprising:
   a housing unit formed therein with a first accommodation space;
   a thermal insulation unit provided within the first accommodation space and formed therein with a second accommodation space;
   a heat conducting unit provided within the second accommodation space and formed therein with a third accommodation space and provided therein with a gas pas- sage channel connected with the third accommodation space which is configured to accommodate the whole of a gas sensor module;

a heater provided on a surface of the heat conducting unit to transfer heat to the heat conducting unit;

a temperature sensor provided inside the heat conducting unit to measure the temperature inside the heat conducting unit in real time; and a control circuitry board electrically connected with the heater and configured to generate a control signal based on the difference between the temperature measured by the temperature sensor and a preset target temperature value so as to keep the temperature inside the heat conducting unit stabilized at the target value all the time.

2. The thermostatic module of the compact gas sensing device according to claim 1, wherein the gas passage channel comprises an inlet passage channel and an outlet passage channel, the inlet passage channel is connected with a gas inlet, the outlet passage channel is connected with a gas outlet, and the third accommodation space is provided between the inlet and the outlet passage channels.

3. The thermostatic module of the compact gas sensing device according to claim 2, wherein the inlet passage channel adopts a sinuous path to achieve a longer heating length within the limited volume of the thermostatic module of the compact gas sensing device compared to a straight one.

4. The thermostatic module of the compact gas sensing device according to claim 3, wherein the inlet passage channel comprises a plurality of straight segments and a plurality of arc-shaped connection segments, the straight segments are arranged in parallel to each other, and each of the arc-shaped connection segments connects its two adjacent straight segments.

5. The thermostatic module of the compact gas sensing device according to claim 1, wherein the housing unit comprises a first housing unit and a second housing unit, the thermal insulation unit comprises a first thermal insulation unit and a second thermal insulation unit, the heat conducting unit comprises a first heat conducting unit and a second heat conducting unit, the first thermal insulation unit is provided inside the first housing unit, the first heat conducting unit is provided inside the first thermal insulation unit, the second thermal insulation unit is provided in the second housing unit, the second heat conducting unit is provided in the second thermal insulation unit, and the first heat conducting unit and the second heat conducting unit are combined and assembled opposite to each other and collectively define the third accommodation space and the gas passage channel.

6. The thermostatic module of the compact gas sensing device according to claim 5, wherein a first sealing member is provided between the first heat conducting unit and the second heat conducting unit to form a good seal along the perimeter of the joining faces of the two heat conducting units.

7. The thermostatic module of the compact gas sensing device according to claim 5,
wherein the surfaces of the first and the second heat conducting units that face each other are coated with polytetrafluoroethylene; or
the surfaces of the first and the second heat conducting units that face each other are silanized.

8. The thermostatic module of the compact gas sensing device according to claim 1, further comprising a gas pump connected to the gas passage channel.

9. The thermostatic module of the compact gas sensing device according to claim 1, wherein the heater is in the form of a heating sheet or wire, and is thermally bonded to the heat conducting unit.

10. The thermostatic module of the compact gas sensing device according to claim 1, wherein when the heater does not perform heating, the temperature measured by the temperature sensor is T1, the target temperature preset by the control circuitry board is T2, T2 and T1 always satisfy T2>T1.

11. The thermostatic module of the compact gas sensing device according to claim 1, wherein the heat conducting unit is made of metal, metal alloy, or non-metallic materials with good thermal conductivity.

12. A compact gas sensing device, comprising:
the thermostatic module according to claim 1; and
a gas sensor module provided with a power supply and signal transmission circuitry board thereof, wherein both of the gas sensor module and the power supply and signal transmission circuitry board are accommodated within the third accommodation space.

13. The compact gas sensing device according to claim 12, wherein a first electric cable is provided between the heater and the control circuitry board, and the first electric cable has one end connected with the control circuitry board and the other end passing through the housing unit and the thermal insulation unit and connected with the heater.

14. The compact gas sensing device according to claim 12, wherein a second electric cable is provided between the power supply and signal transmission circuitry board of the gas sensor module and an external power supply and signal acquisition system, and a second sealing member made of elastic rubber materials is provided between the second electric cable and the heat conducting unit to secure a good seal.

* * * * *